(12) United States Patent
Merchant et al.

(10) Patent No.: US 8,864,747 B2
(45) Date of Patent: Oct. 21, 2014

(54) POWER ASSISTED LIPOPLASTY

(75) Inventors: Adnan I. Merchant, Fremont, CA (US);
David B. Mogill, Westminster, CO (US);
Wayne A. Siebrecht, Golden, CO (US)

(73) Assignee: Sound Surgical Technologies LLC, Louisville, CO (US)

(*) Notice: Subject to any disclaimer, the term of this patent is extended or adjusted under 35 U.S.C. 154(b) by 275 days.

(21) Appl. No.: 13/249,113

(22) Filed: Sep. 29, 2011

(65) Prior Publication Data
US 2012/0078234 A1    Mar. 29, 2012

Related U.S. Application Data

(60) Provisional application No. 61/387,978, filed on Sep. 29, 2010.

(51) Int. Cl.
*A61M 27/00* (2006.01)
*A61B 17/32* (2006.01)
*A61M 1/00* (2006.01)

(52) U.S. Cl.
CPC ........ *A61B 17/32002* (2013.01); *A61M 1/0039* (2013.01); *A61M 2202/08* (2013.01)
USPC ............................................ 604/542; 604/22

(58) Field of Classification Search
USPC ................... 604/22, 540–543, 30, 31, 27, 28; 606/169–171
See application file for complete search history.

(56) References Cited

U.S. PATENT DOCUMENTS

| 5,653,698 A | 8/1997 | Niedospial et al. |
| 5,980,545 A * | 11/1999 | Pacala et al. .................. 606/170 |
| 6,258,054 B1 * | 7/2001 | Mozsary et al. ................ 604/22 |
| 2008/0319468 A1 * | 12/2008 | Shabaz et al. ................. 606/171 |

OTHER PUBLICATIONS

International Search Report dated Jan. 17, 2012, issued in Application Serial No. PCT/US2011/54041, 8 pp.

* cited by examiner

*Primary Examiner* — Tatyana Zalukaeva
*Assistant Examiner* — Benedict L Hanrahan
(74) *Attorney, Agent, or Firm* — Wood, Herron & Evans LLP

(57) ABSTRACT

Described are embodiments that include a device with a motor that when connected to a cannula rotates the cannula while removing adipose tissue from a surgical site. The device provides a direct pathway, for aspirated adipose tissue, from a tip of the cannula to a location where tubing is attached to the device. The pathway does not pass through the motor that provides the angular rotation of the cannula. Instead, the path for the adipose tissue passes through a removable coupler that is connected to the cannula. The embodiments provide a cannula that rotates but also has a direct flow path for adipose tissue that does not pass through the motor.

10 Claims, 16 Drawing Sheets

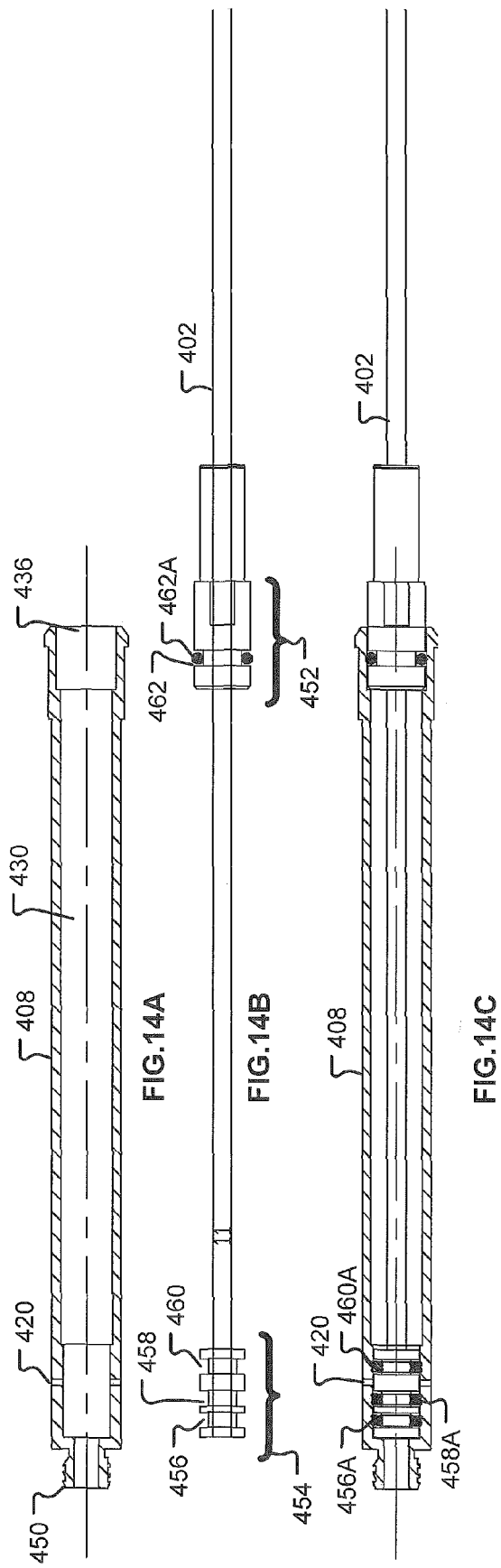

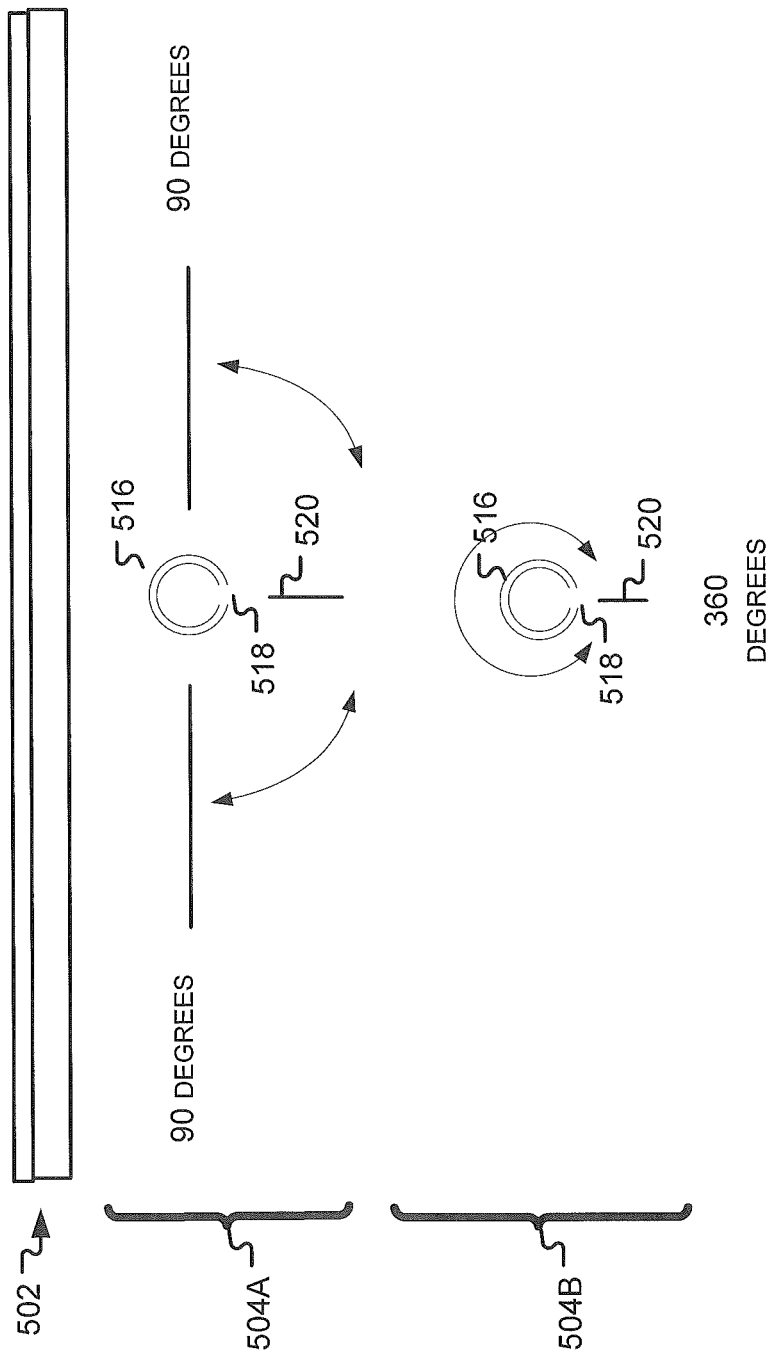

POWER ASSISTED LIPOPLASTY

CROSS-REFERENCE TO RELATED APPLICATIONS

This application claims priority to U.S. Provisional Patent Application No. 61/387,978, filed Sep. 29, 2010, entitled POWER ASSISTED LIPOPLASTY, which is hereby incorporated by reference in its entirety as if set forth herein in full.

FIELD

Embodiments of the present invention relate generally to medical methods and devices. In particular, embodiments relate to methods and devices for use in power assisted lipoplasty.

BACKGROUND

Lipoplasty is a medical procedure that involves removal of adipose tissue from a human patient. There are several different types of lipoplasty procedures that have particular steps for making the removal of the adipose tissue more efficient, effective, or safe. For example, ultrasonic assisted lipoplasty (UAL) utilizes ultrasonic energy. In UAL, a surgical site, with adipose tissue, is first infiltrated with an infiltrate solution. After infiltration, ultrasonic energy is applied to the surgical site using a probe that conducts ultrasonic energy. After the ultrasonic energy has been applied to the surgical site, the adipose tissue is then aspirated (removed using a vacuum).

Power assisted lipoplasty is another type of lipoplasty procedure. Power assisted lipoplasty procedures involve the use of mechanical movement during aspiration of adipose tissue from a surgical site. Power assisted lipoplasty may be combined in some cases with aspects of UAL. Power assisted lipoplasty is typically performed using a cannula that moves during aspiration. For example, MicroAire, of Charlottesville, Va. manufactures a device for use in power assisted lipoplasty. The MicroAire device is a cannula that moves back and forth along a center axis of the cannula, i.e., with a "jack hammer" like movement, during aspiration. Such devices are not ideal because inexperienced users may puncture muscle tissue or skin if they move the cannula too close to the skin layer or muscle layer.

Another company Kolster Methods Inc., (KMI) of Corona, Calif. sells a cannula for use in power assisted lipoplasty that rotates about the center axis of the cannula. This is an improvement because the movement is angular instead of axial. In the device that KMI sells, the flow path of adipose tissue being aspirated passes through the motor. The device must be autoclaved after each use. The motor in the KMI device degrades in the autoclave and thus cannot be used for very many procedures as a result of premature failure. KMI also owns U.S. Pat. Nos. 6,638,238 and 6,875,207 that generally describe a device that is powered by vacuum energy, the vacuum also being used to aspirate tissue. What is needed is a device that provides movement during aspiration of adipose tissue from a surgical site but does not have axial movement and may be used a relatively large number of times.

SUMMARY

This summary is provided to introduce a selection of concepts in a simplified form that are further described below in the Detail Description section. This summary is not intended to be used as an aid in determining the scope of the claimed subject matter.

Described are embodiments that include a device with a motor that is configured to rotate a cannula while removing adipose tissue from a surgical site by aspiration. The rotational movement, which is powered mechanically rather than by a vacuum, assists in removing the adipose tissue from the surgical site. Additionally, the device provides a direct pathway, for aspirating adipose tissue, from a tip of the cannula to a location where tubing is attached. The pathway does not pass through the motor that provides the angular rotation of the cannula. Instead, the path for the adipose tissue passes through a removable coupler that is connected to the cannula. The cannula includes a first gear that is connected to a second gear that is rotated by the motor. This allows the cannula to rotate but also have a direct flow path for adipose tissue that does not flow through the motor. In embodiments, the flow path is also used for infiltrating tissue with fluids. In embodiments, the motor is rated for autoclave sterilization and therefore may be sterilized a large number of times before degrading.

BRIEF DESCRIPTION OF THE DRAWINGS

Non-limiting and non-exhaustive embodiments are described with reference to the following figures.

FIG. 14 illustrates another embodiment of a coupler and cannula that may be used for infiltration of adipose tissue.

FIG. 16 illustrates embodiments of different angular rotations of a cannula when aspirating adipose tissue from different locations in a patient.

DETAILED DESCRIPTION

Various embodiments are described more fully below with reference to the accompanying drawings, which form a part hereof, and which show specific exemplary embodiments for practicing the invention. However, embodiments may be implemented in many different forms and should not be construed as limited to the embodiments set forth herein; rather, these embodiments are provided so that this disclosure will be thorough and complete, and will fully convey the scope of the invention to those skilled in the art. Embodiments may be practiced as methods, systems or devices. Accordingly, embodiments may take the form of a hardware implementation, an entirely software implementation or an implementation combining software and hardware aspects. The following detailed description is, therefore, not to be taken in a limiting sense.

Described are embodiments that are useful for removing tissues and fluids from patients using a rotating cannula. In some embodiments, the rotation of the cannula effects fragmentation (e.g., break up) of tissues that are then removed by aspiration through the cannula. In one specific embodiment, the device is used in Power Assisted Lipoplasty (PAL) for fragmenting and removing tissue from a surgical location. Although the description below focuses on the use of embodiments in PAL, other embodiments are not limited thereto. The description of the embodiment for use in PAL is provided for illustrative purposes only.

Figure 1:
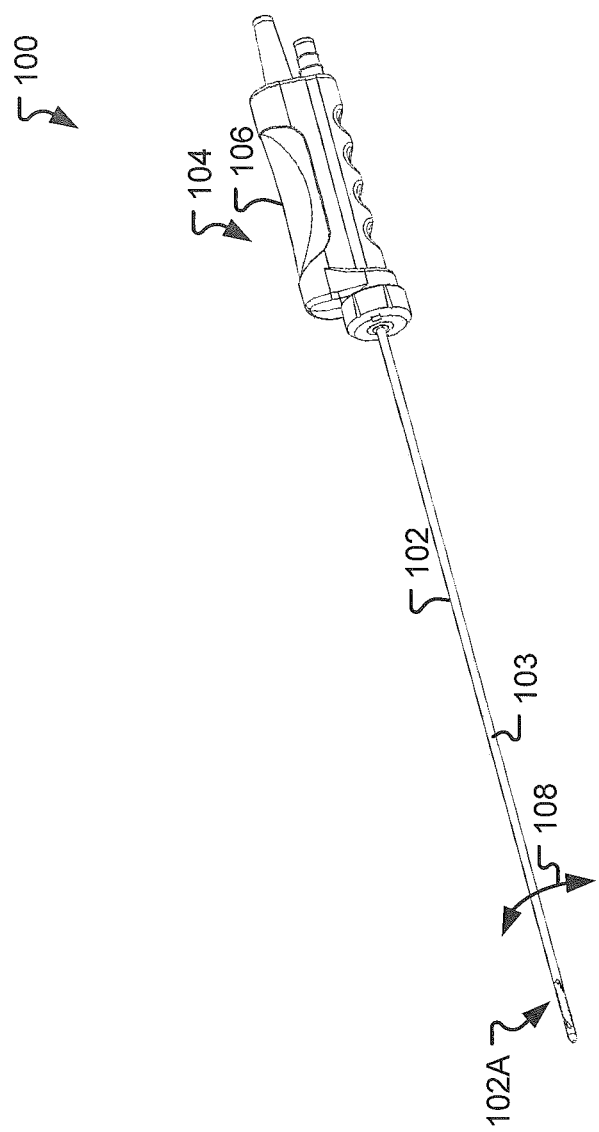
FIG. 1 illustrates a side perspective view of a device used in power assisted lipoplasty designed consistent with an embodiment of the present invention.

FIG. 1 illustrates a side perspective view of a device 100 used in power assisted lipoplasty designed consistent with an embodiment of the present invention. As shown in FIG. 1, device 100 includes a cannula 102 with perforations 102A. Adipose tissue is aspirated from a surgical site by being drawn into perforations 102A and channel 103 of cannula 102 when a vacuum is applied. Cannula 102 is used to provide a pathway for removing adipose tissue from a surgical site to a collection container and to provide a pathway for infiltration fluid delivered to a surgical site from a container.

Device 100 also includes a handpiece 104 that is used by a user to manipulate cannula 102 within a surgical site inside a patient. Handpiece 104 includes a motor 106 that provides the mechanical movement of cannula 102. In particular, motor 106 rotates cannula 102 in a clockwise and/or counter clockwise direction(s) shown by arrows 108. The rotation assists in fragmenting, e.g., breaking up, adipose tissue at a surgical site, which can then be aspirated through the cannula. The degree of rotation of the cannula depends on the actual implementation. In some embodiments, the cannula 102 may rotate more than about 90 degrees (90°), more than about 180° or even more than about 360° in one direction (e.g., clockwise) followed by movement of more than about 90°, more than about 180° or even more than about 360° in the other direction (e.g., counter clockwise). However, in other embodiments the cannula 102 may rotate less than about 360° in at least one direction before changing directions and rotating less than about 360° in the other direction. As those with skill in the art will appreciate, motor 106 may be configured to rotate cannula 102 any desired amount in different directions.

Motor 106 is also configured to rotate cannula 102 at different rotational speeds ranging from about 50 revolutions per minute (rpm) to about 500 rpm. In one embodiment, the speed of the cannula ranges from about 100 rpm to about 420 rpm and motor 106 is configured to be adjusted in increments of about 80 rpm. For example, the motor 106 may be set to rotate the cannula at about 100 rpm, about 180 rpm, about 260 rpm, about 340 rpm, or about 420 rpm. This is merely one embodiment and motor 160 may be adjusted in any increments, in other embodiments.

Figure 2:
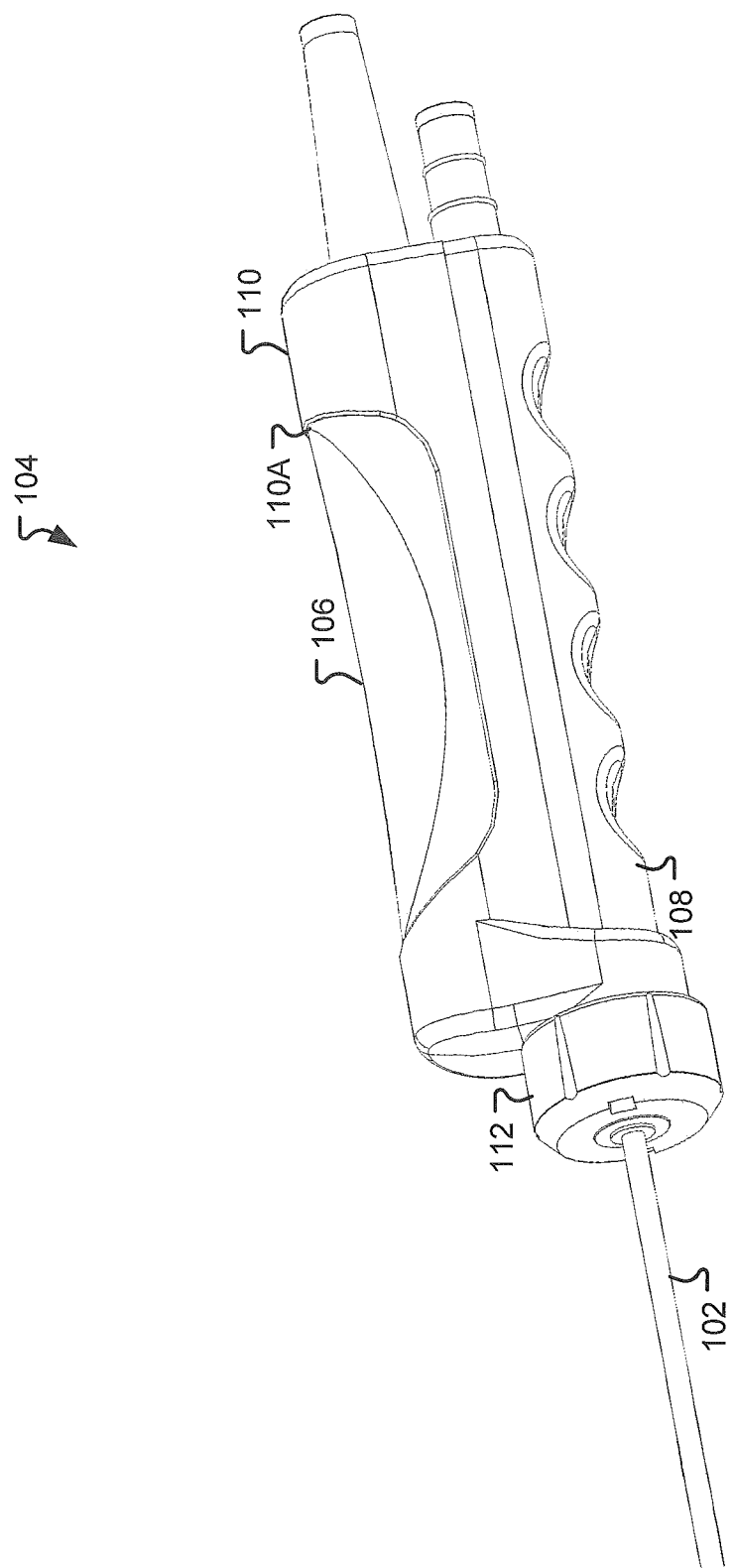
FIG. 2 illustrates a side perspective view of a handpiece of the device shown in FIG. 1.

FIG. 2 illustrates a side perspective view of the handpiece 104 of the device 100 shown in FIG. 1. Shown in FIG. 2 is removable coupler 108 that is part of handpiece 104. Coupler 108 is connected to cannula 102 and provides a pathway for adipose tissue that is aspirated from the surgical site or for infiltration fluid delivered to a surgical site. Hub 112 covers the connection between cannula 102 and coupler 108. Also shown in FIG. 2 is housing 110 which partially covers motor 106 and also provides a portion of the mechanism for connecting motor 106 to removable coupler 108. In the embodiment shown in FIG. 2, housing 110 includes an opening 110A that exposes at least a portion of the motor 106.

Figure 3:
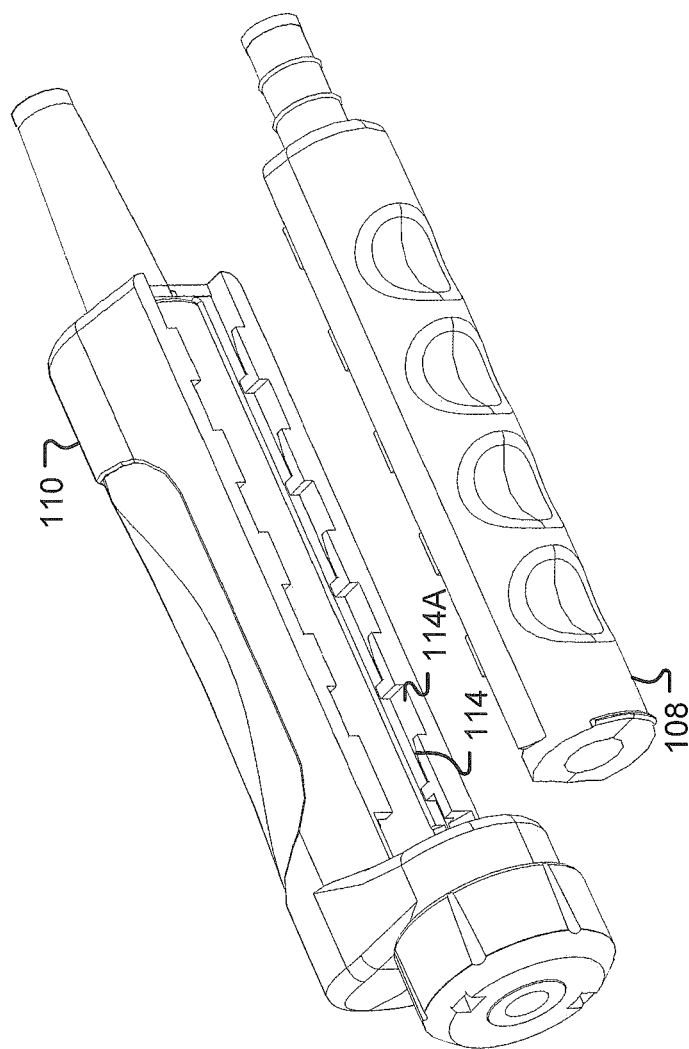
FIG. 3 illustrates a side perspective view of the handpiece shown in FIG. 2 with a motor and a removable coupler of the handpiece separated.
Figure 4:
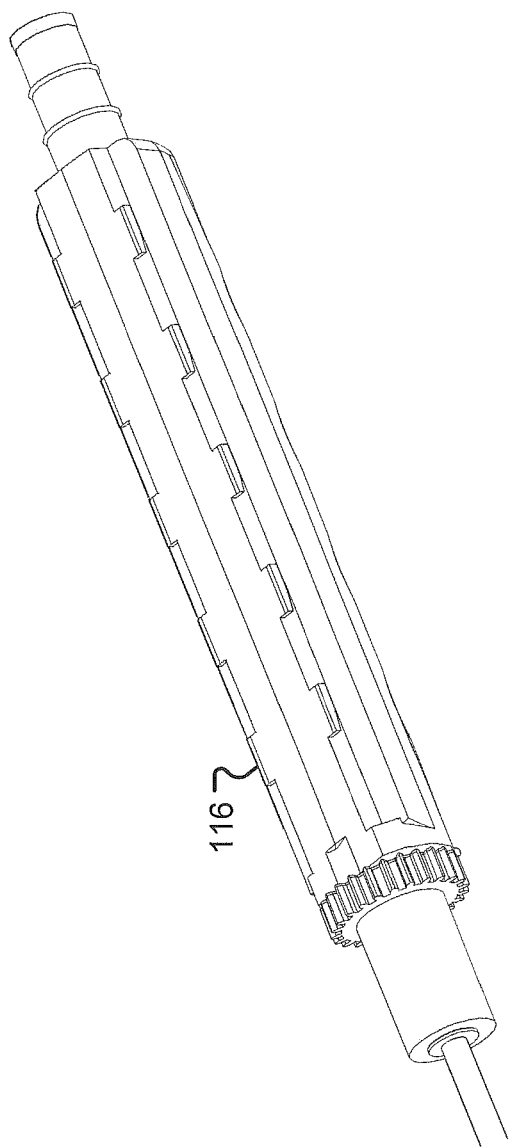
FIG. 4 illustrates a top perspective view of the cannula hub and removable coupler of the handpiece shown in FIG. 2.
Figure 11:
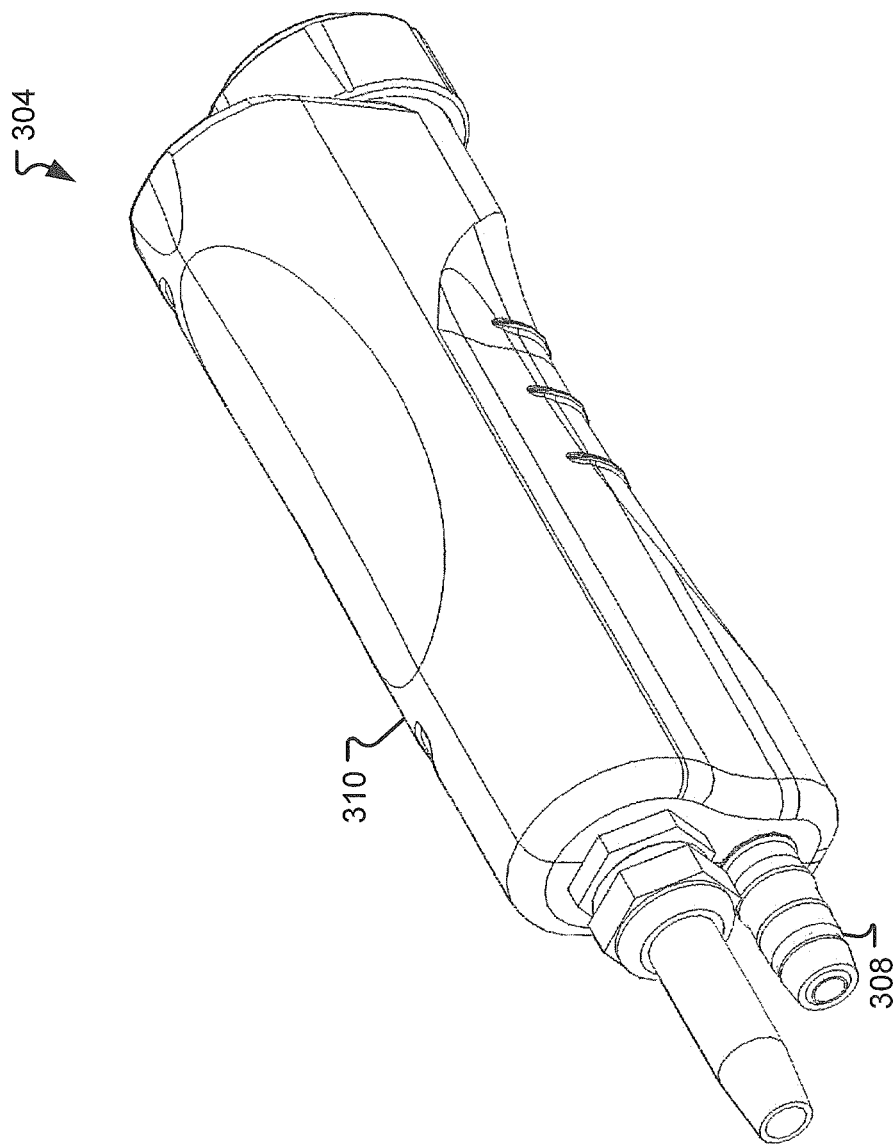
FIG. 11 illustrates a side perspective view of a second embodiment of a handpiece.
Figure 12:
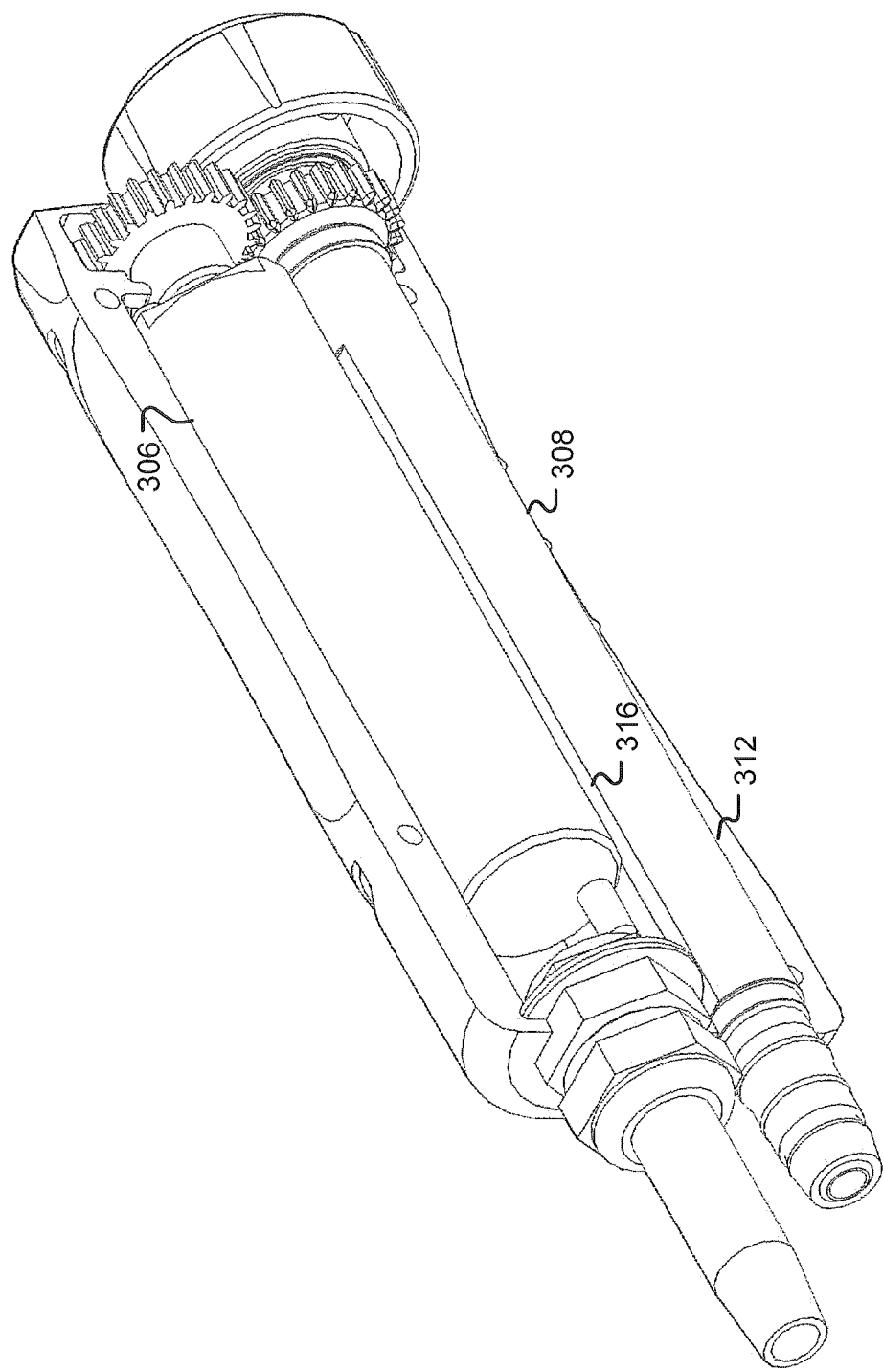
FIG. 12 illustrates a side perspective view of the handpiece shown in FIG. 11 exposing the interior of the handpiece.
Figure 13:
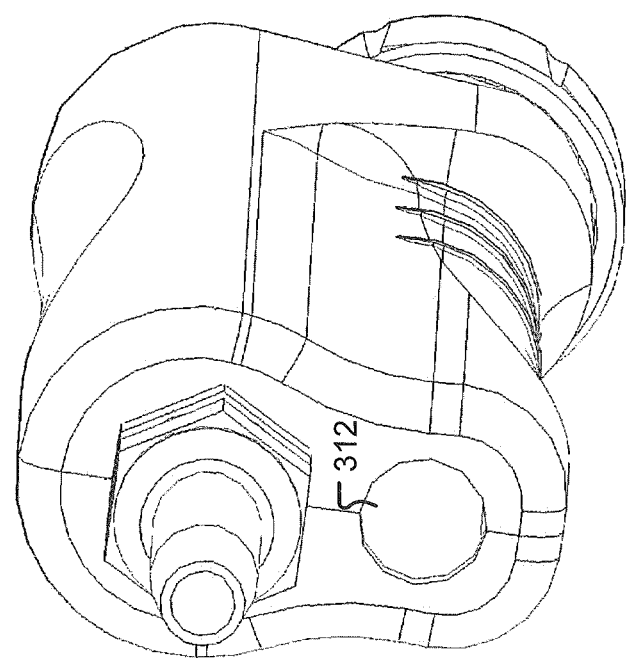
FIG. 13 illustrates a rear perspective view of the handpiece shown in FIG. 11 showing the channel within the housing when the removable couple is removed.

FIG. 3 illustrates the features of housing 110 that are used to connect motor 106 to removable coupler 108. As shown in FIG. 3, housing 110 includes a number of channels 114 that engage tabs on removable coupler 108. Channels 114 include openings 114A that allow tabs to be initially positioned within the channels 114. The tabs can then be slid and secured within channels 114. FIG. 4 illustrates a top perspective view of the removable coupler 108 and cannula hub and shows the tabs 116 that are positioned within the channels 114 and used to engage coupler 108 with housing 110. It should be understood that the mechanism shown in FIGS. 3 and 4 for connecting the removable coupler 108 with the motor 106 is presented merely for illustrative purposes. Any mechanism that connects motor 106 to removable coupler 108 yet still allows removable coupler 108 to be separated from motor 106 may be used with the present invention. In some embodiments, there may not be a housing such as housing 110, and instead motor 106 may include other features and mechanisms, such as bracket, fasteners, and/or clamp, for connecting motor 106 to removable coupler 108. FIGS. 11-13, described below, illustrate an alternative embodiment for connecting a coupler to a motor.

Figure 5:
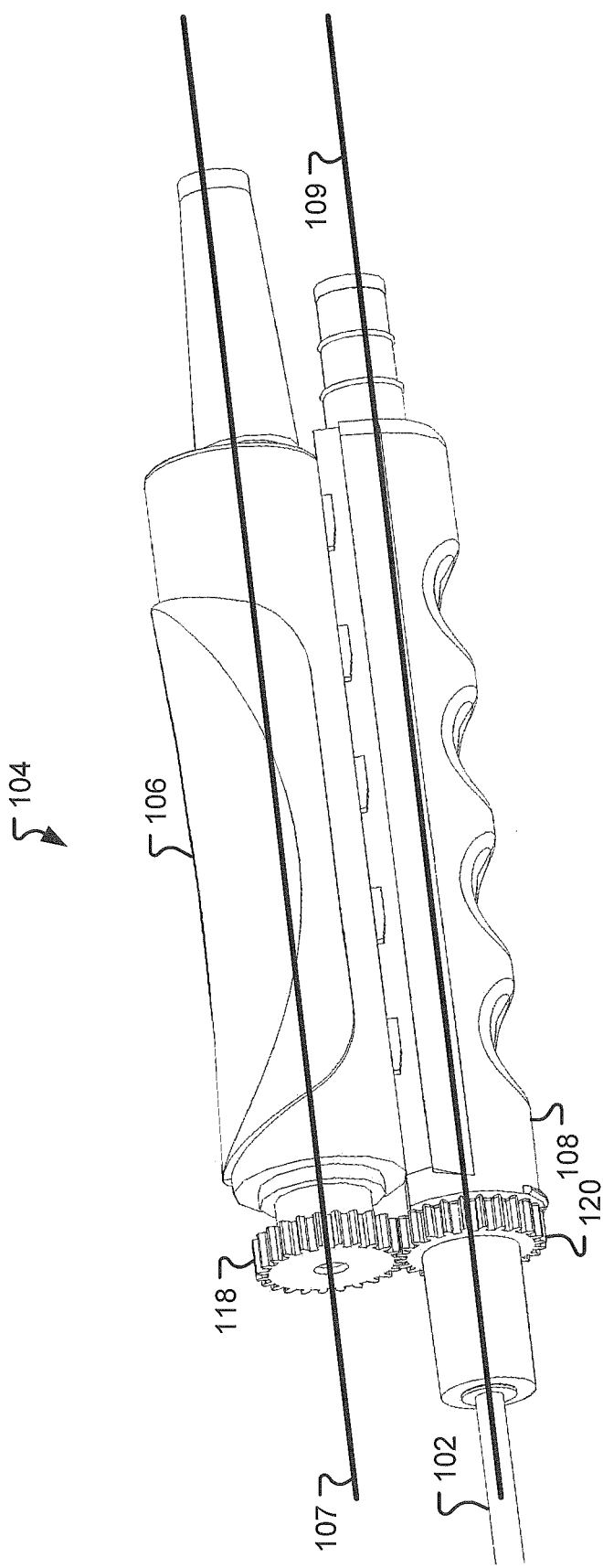
FIG. 5 illustrates a side perspective view of the handpiece shown in FIG. 2 without the outside shell 110, or hub 112.

FIG. 5 illustrates a side perspective view of the handpiece 100 shown in FIG. 2, without the outside shell 110 or hub 112. FIG. 5 illustrates features of embodiments of the present invention. As shown in FIG. 5 motor 106 is located on the side of coupler 106 and cannula 102, yet still rotates cannula 102. In this design, the flow path for the adipose tissue is through cannula 102 and removable coupler 108. The pathway does not pass through motor 106. This design is distinct from available devices in which the flow path for the adipose tissue passes through the motor that rotates the cannula. As shown in FIG. 5, a center axis 107 of motor 106 does not coincide with a center axis of removable coupler 109, which is also the center axis of cannula 102 when connected to coupler 109. In embodiments, center axis 107 is substantially parallel to axis 109. In other embodiments, axis 107 may not be substantially parallel to axis 109 as shown in FIG. 5 but may be positioned at some angle relative to axis 109. However, even in these embodiments, axis 107 does not substantially coincide with the flow path of adipose tissue removed from a surgical site. As previously noted, the flow path is also used in embodiments for delivering infiltration fluid to a surgical site.

In embodiments, motor 106 is an electric motor. Use of an electric motor as motor 106 may provide improvements over other devices that use vacuum driven motors. Electric motors are more reliable, more user friendly, and are easier to miniaturize to fit within a handpiece.

Figure 6:
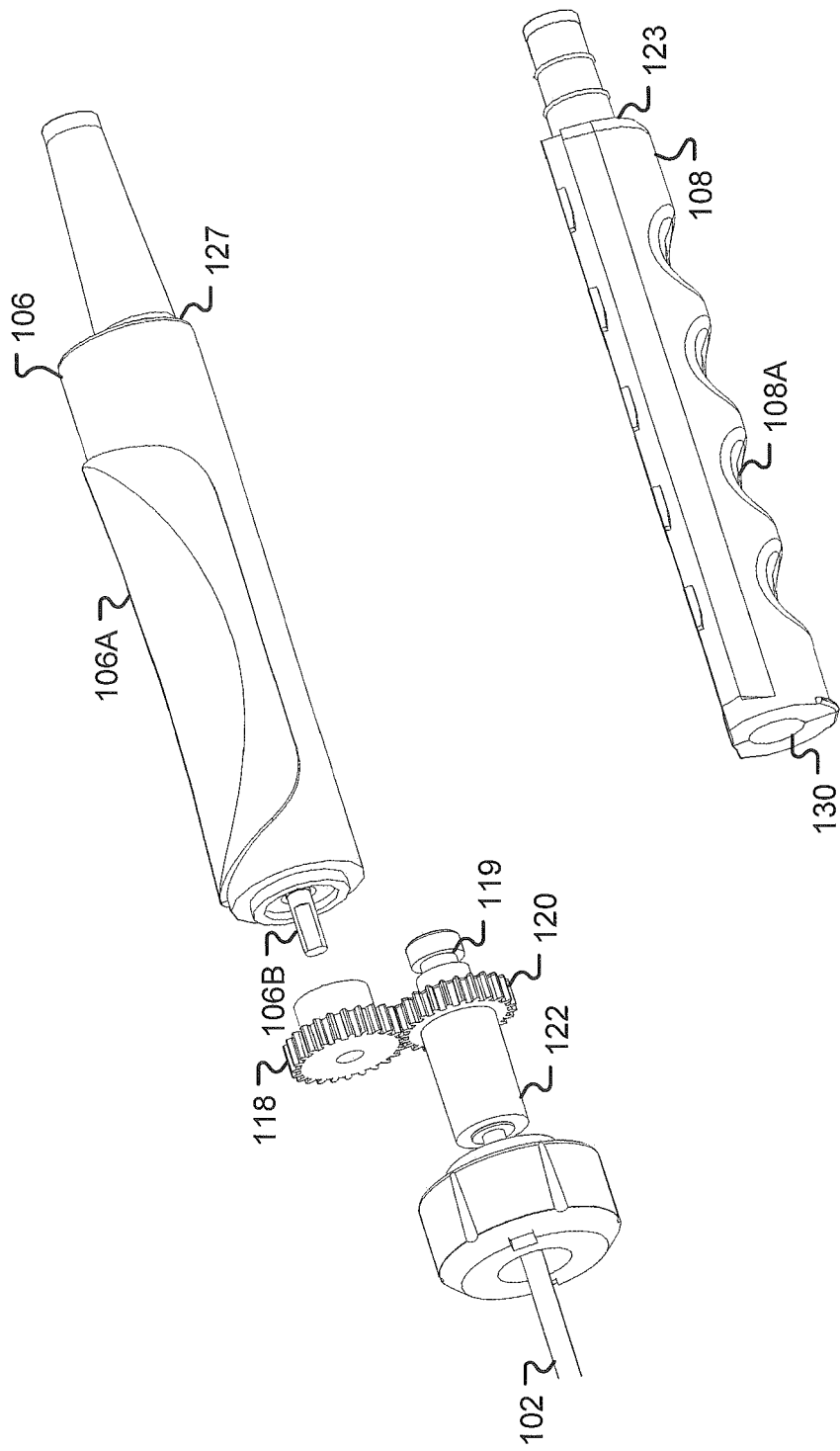
FIG. 6 illustrates a side exploded view of the handpiece shown in FIG. 2 without the outside shell 110, or hub 112.

FIG. 6 illustrates a side exploded view of the handpiece shown in FIG. 5 without the outside shell 110 and with hub 112. FIG. 6 illustrates the components used to transfer the motion from motor 106 to the cannula 102. Motor 106 includes a shaft 106B which rotates. Connected to shaft 106B is gear 118 which engages gear 120. Gear 120 is connected to cannula 102. Gears 118 and 120 transfer the rotational motion of shaft 106B of motor 106 to cannula 102. It is noted that although FIG. 6 illustrates only two gears, other embodiments may include more complicated designs with additional gears, shafts, pulleys, or other mechanical components for transferring motion from motor 106 to rotation of a cannula. In one embodiment, gear 118 is connected to additional components which then transfer the movement of gear 118 to gear 120.

Also shown in FIG. 6 are ergonomic features that are incorporated into portions of the handpiece 104. For example, motor 106 includes an outside surface 106A that may be molded with material such as silicone to allow a user to more comfortably grip handpiece 104. Additionally, the molded material may have some ornamental features. Removable coupler 108 also includes indentations 108A that can accommodate the fingers of a user. The indentations 108A can be customized or standardized. Outside surface 106A and indentations 108A are merely some examples of ergonomic features that may be incorporated into handpiece 100. Those with skill in the art will appreciate that additional features may be added in other embodiments.

FIG. 6 also shows is a grove 119 on the back end of cannula 102. Groove 119 in embodiments is used to secure an o-ring onto cannula 102. The o-ring helps to provide a seal between the cannula 102 and a channel 130 of removable coupler 108, helping to maintain a vacuum.

In some embodiments, the motor 106 may include a swivel mechanism at location 127 that allows the motor 106 to rotate with respect to the cable. This is useful so that a user does not have to work against the resistance of the cable when manipulating the handpiece, which reduces the strain on a users hand or wrist. The removable coupler may also include a swivel mechanism at location 123 that also allows the coupler to rotate with respect to tubing connected to the coupler 108. This also reduces the strain on a user.

Figure 7:
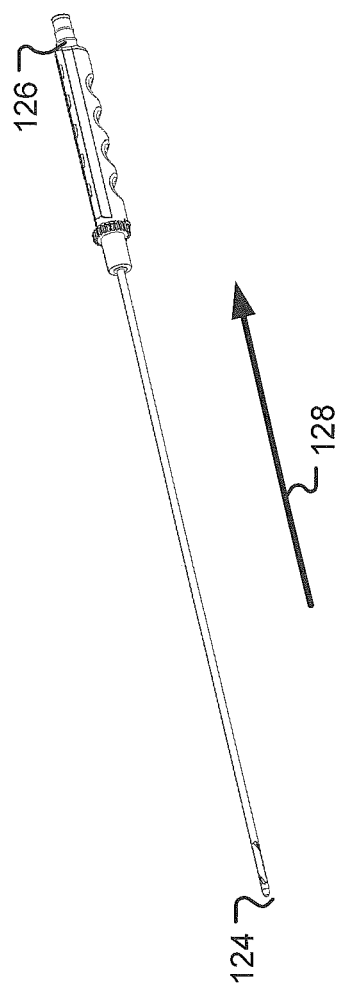
FIG. 7 illustrates a side perspective view of the removable coupler 108 connected to the cannula showing the direct path provided for flow of adipose tissue.

FIG. 7 illustrates a side perspective view of the removable coupler 108 connected to the cannula showing the direct path provided for flow of adipose tissue. One feature of embodiments of the present invention is the ability to provide a direct path from a tip 124 of the cannula 102 where adipose tissue enters the cannula 102 to a location 126 where tubing that provides the vacuum is connected to the handpiece. FIG. 7 illustrates the flow of adipose tissue in the direction noted by arrow 128. As shown in FIG. 7 there is a direct path from tip 124 to location 126. When coupler 108 is connected to cannula 102, channel 103 of cannula 102 is substantially collinear with a channel 130 (FIG. 8) of coupler 108. It is noted that in some embodiments, the channel 103 of cannula 102 or the channel 130 of the removable coupler 108 may not be substantially straight, but may include some curves or twists. In those embodiment in which coupler 108 and cannula 102 are used to deliver infiltration fluid to a surgical site, the flow of fluid is opposite the direction noted by arrow 128.

A handpiece with a flow path that does not pass through motor 106 provides a number of improvements over handpieces in which the flow path of adipose tissue (or infiltration fluid) does pass through a motor. As one example, a leak in the portion of the flow path that passes through the motor can damage the motor, which requires replacement of the entire handpiece. Also, leaks in the portion of the flow path that passes through the motor are not easily repaired. Thus, even if the leaks do not immediately damage the motor, the handpiece may need to be replaced because of the difficulty in repairing the leaks or breaks in the portion of the flow path that passes through the motor. In contrast, having the flow path pass through the removable coupler 108, allows easy replacement of the removable coupler in the event of any leaks or breaks. Also, the motor 106 can be sealed so that any fluid that leaks from a broken coupler does not enter the motor 106.

Figure 8:
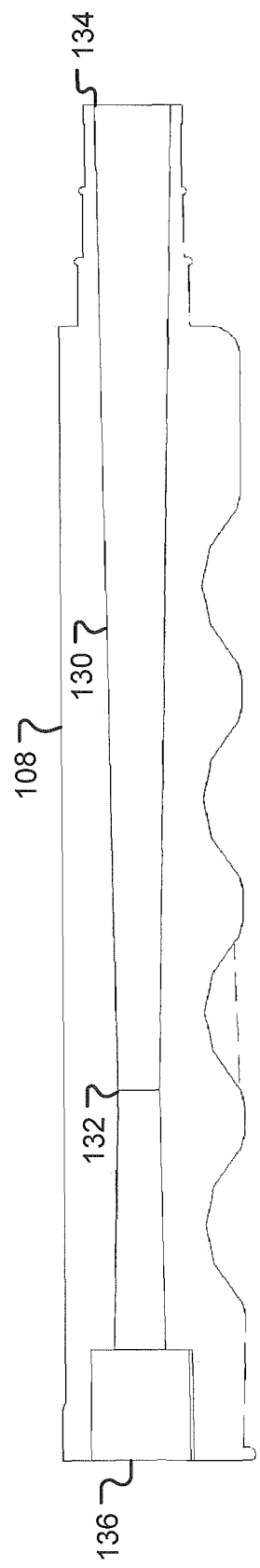
FIG. 8 illustrates a cross-sectional view of the removable coupler 108 cross-sectioned parallel to a central axis of the removable coupler 108.

As those with skill in the art will appreciate, some lipoplasty procedures involve not only removing adipose tissue from the surgical site but reintroducing adipose tissue to other surgical sites within a patient. In these instances, it is important not to damage the cells within the adipose tissue so that they may survive when introduced into the patient. FIG. 8 illustrates a feature of some embodiments that helps to preserve the adipose tissue that is removed from the surgical site. FIG. 8 illustrates a cross-sectional view of the removable coupler 108 cross-sectioned parallel to a central axis of the removable coupler 108. As can be seen in FIG. 8, removable coupler 108 includes a central channel 130 that provides the pathway for adipose tissue. When coupler 108 is connected to a cannula such as cannula 102, channel 130 is substantially collinear with the channel 103 of cannula 102 (see FIG. 7). As shown in FIG. 8, channel 130 is in embodiments tapered. That is, the diameter 132 at one end of channel 130 is less than the diameter 134 at a second end of channel 130. The taper of channel 130 reduces the velocity of the adipose tissue as it flows through channel 130 across the length of the removable coupler 108. The reduction in velocity may help to reduce damage that is done to the cells as they flow through coupler 108. The adipose tissue may then provide better results when introduced into a patient. FIG. 8 also shows a cavity 136 where the cannula 102 is connected to the removable coupler 108.

Figure 9:
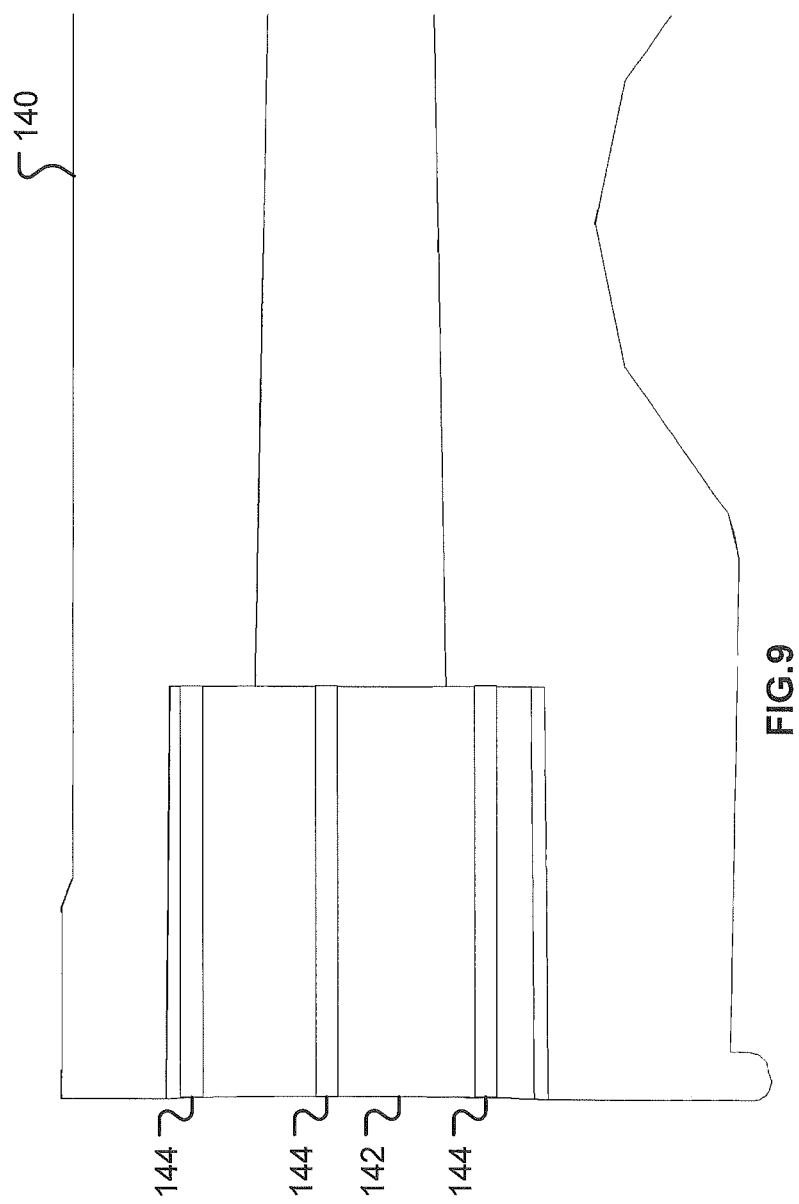
FIG. 9 illustrates a cross-sectional view of an embodiment of a removable coupler that includes channels for controlled venting.

FIG. 9 illustrates a cross-sectional view of an embodiment of a removable coupler 140 that includes channels for controlled venting. The removable coupler 140 includes a cavity 142 (similar to cavity 136 of coupler 108) where a cannula can be connected to the removable coupler 140. For example, cannula 102 with groove 119, and an o-ring positioned within groove 119, can be positioned within cavity 142. Along the interior walls of cavity 142 are venting channels 144 that allow air to flow between the interior walls of cavity 142 and a cannula that is positioned within cavity 142. The venting channels 144 are designed to allow a certain amount of air to flow between the interior walls of cavity 142 and a cannula or an o-ring on the cannula. This controlled venting allows continual flow along a pathway between a surgical site and a collection container for collecting adipose tissue removed from the surgical site. Even if adipose tissue blocks the pathway upstream of the vents, the venting feature allows a continual flow of material from the surgical site to the collection container. As those with skill in the art will appreciate, the combination of venting and a rotating cannula is not found in conventional devices. As can be appreciated, to provide different amounts of venting, venting channels 144 may be of different dimensions, and a coupler may include one or more venting channels 144.

Figure 10:
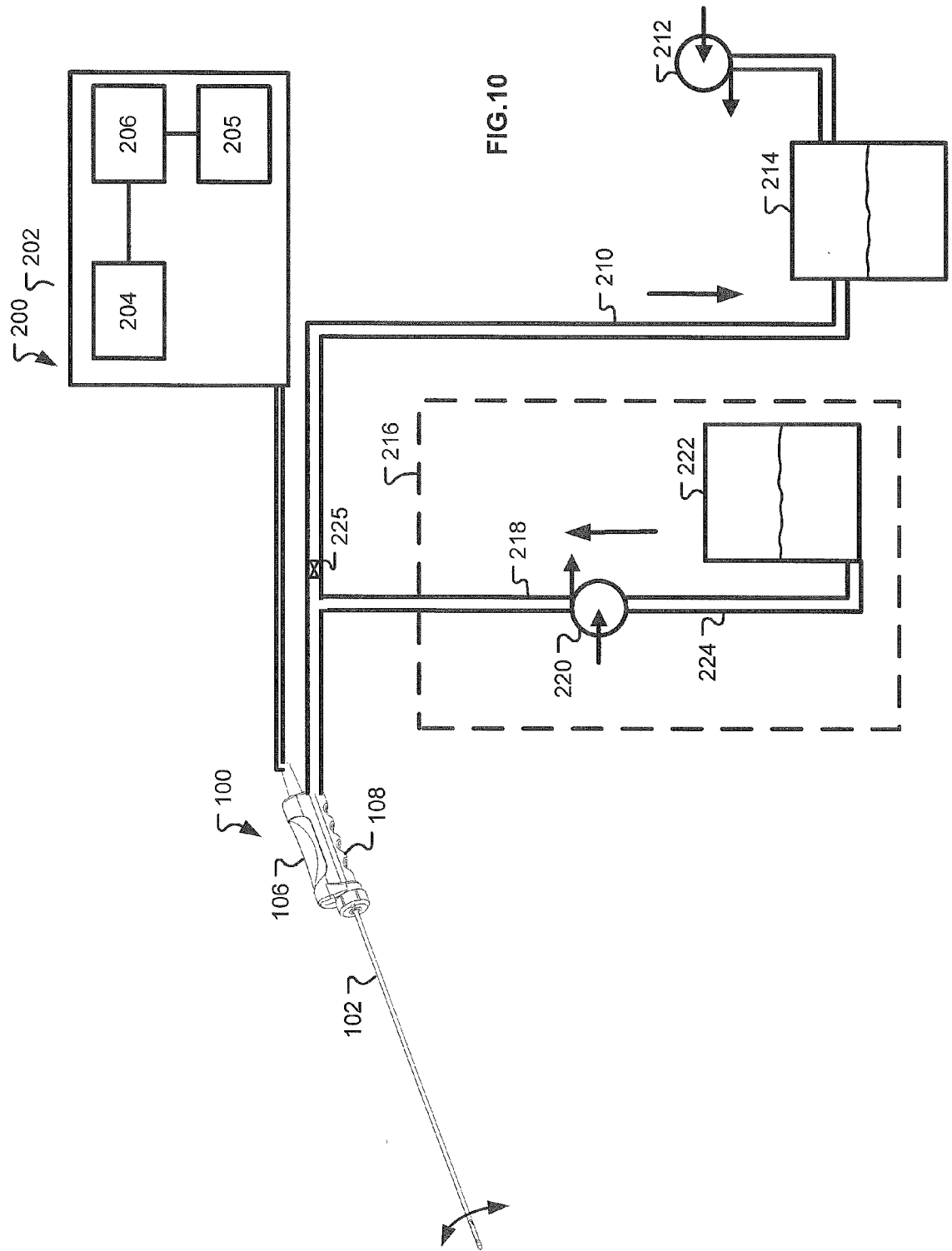
FIG. 10 illustrates a system for aspiration and infiltration that implements the device 100 of FIG. 1.

FIG. 10 illustrates a system 200 in accordance with one embodiment of the present invention. System 200 uses the device 100 of FIG. 1. System 200 also includes a console 202 that is connected to the motor 106 of device 100. The console 202 may include a number of components that helps drive motor 106. For example, console 202 may include a power supply 204 as well as logic 206 for sensing and controlling the amount and direction of rotation of cannula 102. In some embodiments, logic 206 may be hardware or may include aspects of hardware and software. For example in one embodiment logic 206 includes a processor that executes instructions implemented in software. The software is stored in a memory 205 within console 202. The logic 206 can provide precise control over the speed and angular rotation of the cannula 102. The logic 206 can be programmed to change the speed and the amount of rotation based on various factors including, but not limited to, the specific procedure being performed (e.g., infiltration or aspiration), the location of the surgical site, the amount of adipose tissue that will be aspirated, the amount of fluid being used to infiltrate a surgical site, or the type of fluid used to infiltrate a surgical site. This control is distinct from other devices that use a stepper motor that does not require logic to control the rotation of cannula, e.g., an open loop embodiment.

In embodiments, console 202 may provide controls that allow a user to enter settings for the rotation of the cannula. For example, console 202 may include: knobs, buttons, dials, LCD display(s) or other controls that allow a user to enter settings to control logic 206 and ultimately the speed and angle of rotation of cannula 102.

System 200 also includes a pump 214 that creates a vacuum within collection container 214. The vacuum created by pump 214 creates a vacuum within tubing 210, which is connected to the removable coupler 108. The vacuum draws the adipose tissue from the surgical site through cannula 102, coupler 108, tubing 210 and into container 214. The adipose tissue may be store within container 214 until disposed of or further processed for reintroduction into a patient. The vacuum is not used in any way to affect rotation of the cannula.

In some embodiments, system 200 may be used for infiltration as well as aspiration. In these embodiments, system 200 will include optional infiltration system 216, which includes tubing 218 connected to a pump 220. Pump 220 when operated pumps infiltration liquid from reservoir 222 through tubing 224, tubing 218, tubing 210, removable coupler 108, and cannula 102 to the surgical site. A valve 225 may be used to ensure that infiltration liquid does not enter the aspiration system. In these embodiments, cannula 102 may be rotated during infiltration of the surgical site. The rotation of cannula 102 may be in directions and amounts that are different than the rotation of cannula 102 during aspiration. In other embodiments, the rotation of cannula 102 may be the same during infiltration and aspiration.

FIG. 11 illustrates a side perspective view of a second embodiment of a handpiece 304 according to the present invention. Handpiece 304 also includes a removable coupler 308. Handpiece 304 includes a housing 310 that covers a majority of a motor 306 and a majority of the removable coupler 308. As shown in greater detail in FIGS. 12 and 13, removable coupler 308 is positioned within a channel 312 (FIG. 13) of housing 310. FIG. 12 illustrates a side perspective view of the handpiece 304 with a portion of housing 310 missing to expose the interior of the handpiece 304. FIG. 13 illustrates a rear perspective view of the handpiece 304 showing the channel 312 when removable coupler 308 is not positioned within the channel 312.

As shown in FIG. 12, handpiece 304 includes a motor 306 positioned within housing 310. The removable coupler 308 is also positioned within housing 310 in channel 312. The removable coupler 308 can be inserted into, and removed from, channel 312, and when positioned within channel 312 is mechanically secured within channel 312. For example, removable coupler 308 may include one or more ridges along its length that fit within grooves in channel 312. As another example, the removable coupler 308 may include o-rings that contact the interior surface of channel 312 to secure coupler 308 within the channel. These are merely some examples, and any mechanical features for securing coupler 308 in channel 312 may be used. Coupler 308 also includes some anti-rotation features. As shown in FIG. 12, coupler 308 has a flat surface 316 on the top and another flat surface (not shown) on the bottom. The top surface 316 may contact portions of channel 312 and portions of motor 306 to prevent it from rotating when a cannula connected to coupler 308 is being rotated by motor 306.

As can be appreciated by the above description, removable coupler 308 can be easily replaced if there is a break or leak in coupler 308. It is easily removed and replaced. In some embodiments, different couplers may be used with the same handpiece 304. For example, a first coupler may be used when handpiece 304 is used for infiltration of adipose tissues. The first coupler may include features that allow it to easily connect to an infiltration system, or have other features that make it appropriate for use in infiltration of adipose tissues (e.g., FIGS. 14a-14C). A second coupler with different features can then be used when aspirating tissue from a patient.

FIGS. 14A-14C illustrate an embodiment of a coupler 408 and a cannula 402 that are used in some embodiments of the present invention for infiltration of adipose tissue. FIG. 14A illustrates the coupler 408, FIG. 14B illustrates the cannula 402, and FIG. 14C illustrates the cannula 402 when connected to, and positioned within, coupler 408.

As shown in FIG. 14A, coupler 408 includes a channel 430 that is part of a flow path for infiltration fluid. A coupling 450 is used to connect coupler 408 to a source of fluid, such as infiltration system 216 (FIG. 10). In the embodiment shown in FIG. 14A, coupler 450 has threads that allow coupler 408 to connect to the source of infiltration fluid. Coupler 408 also includes a cavity 436 where at least a portion of a cannula, such as cannula 402 connects to coupler 408. A hole 420 is also included in coupler 408. As described in greater detail below with respect to FIG. 14C, the hole 420 allows infiltration fluid to escape the coupler 408 if the cannula 402 is not sealed properly with the coupler 408.

Referring now to FIG. 14B, the cannula 402 includes two hubs 452 and 454. Each of hubs 452 and 454 includes features for creating a seal with cannula 402 and prevent infiltration fluid from leaking. Hub 452 includes a grove 462 into which an o-ring 462A is positioned. Hub 454 includes grooves 456, 458, and 460. As shown in FIG. 14C, o-rings 456A, 458B, and 460C are positioned in grooves 456, 458, and 460 respectively to create a seal between coupler 408 and cannula 402.

As shown in FIG. 14C, cannula 402 slides into channel 430 of coupler 402. When connected to coupler 408, the o-ring 462A contacts and creates a seal with the inside surface of cavity 432. Also, o-rings 456A, 458A, and 460A contact the inside surface of channel 403 and also create a seal. Hole 420 of coupler 408 is positioned between o-rings 458A and 460A. The hole 420 allows any infiltration fluid that leaks around o-rings 456A and 458A to escape and not leak into other areas, such a motor that may be connected to coupler 408.

As can be appreciated, the presence of the two hubs 452 and 454 provides a more robust connection between coupler 408 and cannula 402. When cannula 402 is in use, a moment may be created about a connection point between the coupler 408 and cannula 402. Having two hubs creates two connection points and makes it less likely that the connection, and the seal, between the coupler 408 and cannula 402 will fail.

Although, the cannula 402 and coupler 408 are described as useful for infiltration of adipose tissue. They may be used in embodiments for aspiration of adipose tissue. Features such as having two hubs are also useful when aspirating adipose tissue.

Figure 15A:
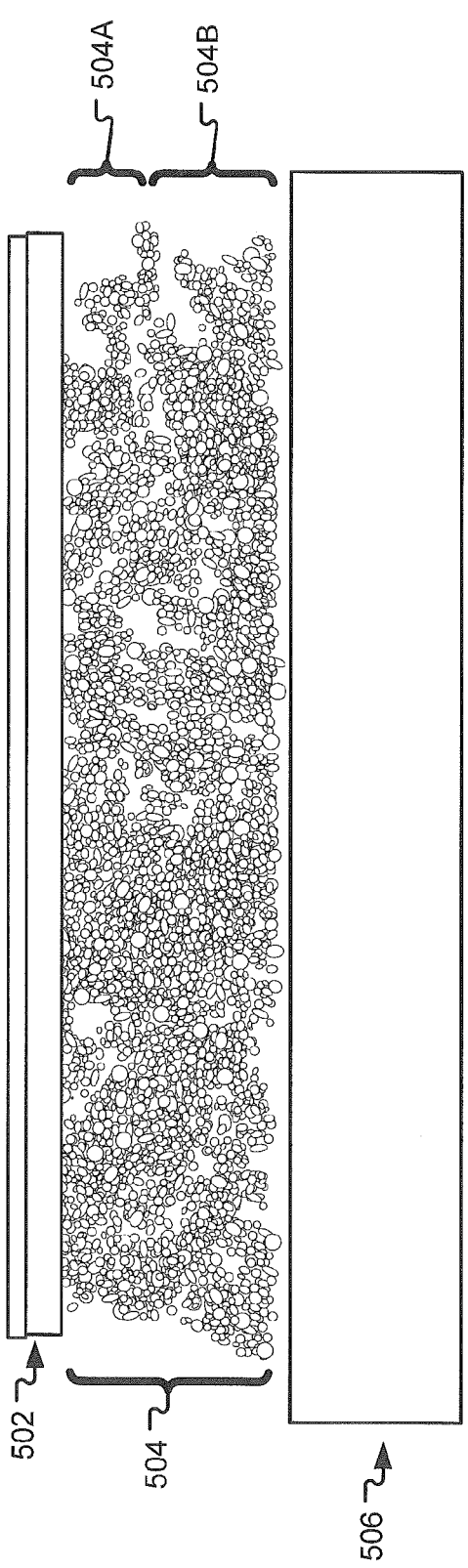
FIGS. 15A and 15B illustrate a portion of a patient's body before and after adipose tissue is removed, e.g., aspirated.
Figure 15B:
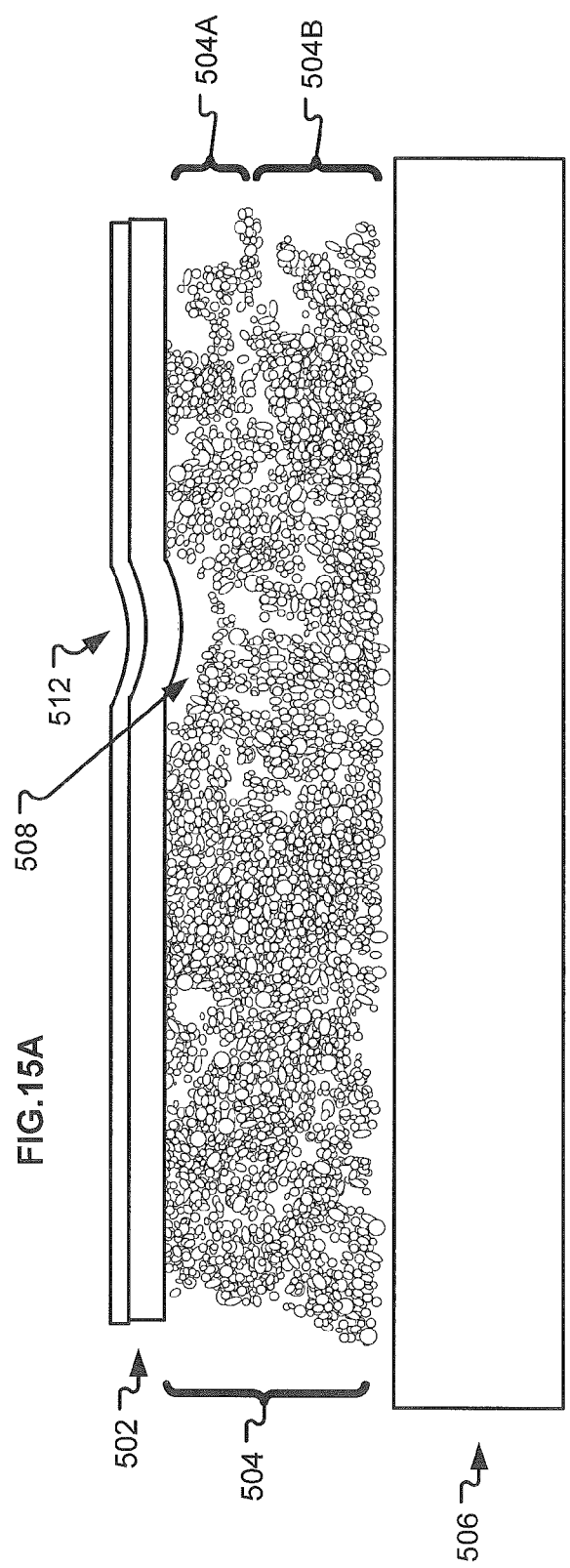

FIGS. 15A and 15B illustrates a portion of a patient's body including layers of skin 502, a subcutaneous layer of fat 504 from which the adipose tissue is removed, and some other anatomical layer 506 (e.g. muscle tissue). Although shown as distinct layers in the drawings, in fact, layers such as 504 and 506 can be interdispersed particularly at their boundary. In FIGS. 15A and 15B, the portion of layer 504 that is near the skin 502 is labeled 504A, while the portion that is deeper is labeled 504B.

FIG. 15A shows an embodiment where no adipose tissue has yet been removed from a patient. FIG. 15B shows that adipose tissue has been removed from a patient's body. In particular, a volume of adipose tissue has been removed from surgical site, location 508, which is in the portion of layer 504 labeled as 504A, near skin 502. As a result of having removed the volume of adipose tissue from location 5 Her08 underneath the skin 502, an indentation 512 has formed on the surface of skin 502. The indentation 508 is not dangerous, but is not aesthetically pleasing. To correct the indentation 512, a surgeon may need to perform some sculpting, i.e. pushing adipose tissue into location 508 as well as remove adipose tissue from surrounding areas near location 508, in order to smooth out the indentation 512. This may prolong the procedure, increasing the time a patient must suffer through some discomfort. As can be appreciated, removing adipose tissue from locations deeper in layer 504, such as portion 504B, is less likely to cause artifacts on the skin surface that affect the appearance of the skin.

In order to avoid creating artifacts on the skin surface, such as indentation 512 shown in FIG. 15B, embodiments of the present invention are designed to prevent the removal of adipose tissue too close to skin 502. Referring now to FIG. 16, two cross-sections of a cannula 516, perpendicular to a center axis of the cannula, are shown. The cross-sections are through a perforation 518 in cannula 516. As can be appreciated, the adipose tissue is removed from a patient through aspiration, namely by applying a vacuum within cannula 516 which causes the adipose tissue to enter cannula 516 through perforation 518. For purposes of illustration, FIG. 16 also shows skin layer 502, and labels 504A and 504B.

The top cross section shown in FIG. 16 illustrate the angle of rotation that the cannula 516 will travel, in one embodiment of the present invention, when adipose tissue is being removed from portion 504A of layer 504. In other words, the surgical site is within portion 504A. As is shown, the cannula is limited in its rotation so that perforation 518 is not allowed to go beyond about 90° from its original position 520 in either clockwise or counterclockwise directions. This limitation prevents adipose tissue from being removed from a location that is too close to skin layer 502, thereby preventing formation of indentations on the surface of skin 502. In these embodiments, the motor, e.g., motor 106 or 306, that is rotating cannula 516 is set so that the rotation of cannula 516 is no more than about 90° in either clockwise or counterclockwise directions. As can be appreciated, in other embodiments, the motor may be set to allow rotation beyond 90° such as about 100° or about 110° but still limit the rotation to prevent adipose tissue from being removed from a location too close to skin 502.

In some embodiments, in addition to limiting the rotation of cannula 516, the motor may also be configured to limit the rotational speed of cannula 516 when removing adipose tissue from layer 504A. The motor may be set to lower speeds, such as from about 100 rpm to about 280 rpm so that there is not as much energy being applied to the adipose tissue near the skin 502. Also, the rate at which the adipose tissue is removed is slower when the cannula is rotated at lower speeds because the adipose tissue is not being fragmented as quickly. This allows a surgeon time to view the skin surface and ensure that it is being contoured as desired by the surgeon. In embodiments, similar angles and speeds are used when infiltrating adipose tissue in portion 504A of layer 504.

The bottom cross section shown in FIG. 16 illustrate the angle of rotation that the cannula 516 will travel, in one embodiment of the present invention, when adipose tissue is being removed from portion 504B of layer 504. That is, the surgical site is within portion 504B. As is shown, the cannula 516 may rotate so that perforation 518 rotates 360° from its original position 520 in either clockwise or counterclockwise directions. When removing adipose tissue from portion 504B, which is deeper in layer 504, there is less risk of creating indentations on the surface of skin 502; as a result the cannula 516 is allowed to rotate 360° to remove adipose tissue all the way around cannula 516. In these embodiments, the motor, e.g., motor 106 or 306, that is rotating cannula 516 is set so that the rotation of cannula 516 is 360°, or more, in either clockwise or counterclockwise directions.

In addition to rotating the cannula 360°, the motor may also be configured to rotate cannula 516 at relatively higher speeds when removing adipose tissue from layer 504B. The motor may be set to speeds, such as from about 360 rpm to about 420 rpm, so that the adipose tissue is fragmented and removed relatively quickly. Removing adipose tissue more quickly from portion 504B shortens the procedure time and may allow a surgeon more time to sculpt the patient when removing tissue closer to skin 502. In embodiments, similar angles and speeds are used when infiltrating adipose tissue in portion 504B of layer 504.

It is noted that the description of FIGS. 14A-15 is made for illustrative purposes only to show combinations of amount of rotation and speeds that a motor consistent with the present invention may implement. As indicated above, motors of the present invention may have a variety of settings for both the amount of rotation and the rotational speed. A surgeon can then decide the appropriate combination of amount and speed for a particular procedure.

Reference has been made throughout this specification to "one embodiment" or "an embodiment," meaning that a particular described feature, structure, or characteristic is included in at least one embodiment. Thus, usage of such phrases may refer to more than just one embodiment. Furthermore, the described features, structures, or characteristics may be combined in any suitable manner in one or more embodiments.

One skilled in the relevant art may recognize, however, that the invention may be practiced without one or more of the specific details, or with other methods, resources, materials, etc. In other instances, well known structures, resources, or operations have not been shown or described in detail merely to avoid obscuring aspects of the invention.

While example embodiments and applications have been illustrated and described, it is to be understood that the invention is not limited to the precise configuration and resources described above. Various modifications, changes, and variations apparent to those skilled in the art may be made in the arrangement, operation, and details of the methods and systems disclosed herein without departing from the scope of the claimed invention

We claim:

1. A method of fragmenting and removing adipose tissue from a surgical site using a cannula and a removable coupler connected to the cannula, the method comprising:
connecting a portion of the cannula to a cavity in a distal end of the removable coupler;
aspirating the adipose tissue from the surgical site with vacuum through a channel of the cannula that is coupled to a first end of a channel of the removable coupler to provide a pathway for flow of the adipose tissue into tubing coupled with a second end of the channel of the removable coupler;

venting the cannula through a plurality of venting channels defined in the interior walls of the cavity;

collecting the adipose tissue in a container coupled by the tubing with the second end of the channel of the removable coupler; and during the aspirating, rotating the cannula using a motor connected to the removable coupler and the cannula, wherein a central axis of the motor is adjacent a central axis of the removable coupler so that the pathway does not pass through the motor.

2. The method of claim 1, further comprising:

infiltrating the adipose tissue with a solution prior to removing the adipose tissue.

3. The method of claim 2, further comprising:

rotating the cannula using the motor when the adipose tissue is infiltrated with the solution.

4. The method of claim 1, wherein the cannula is rotated no more than about 90 degrees in one direction during the aspiration of the adipose tissue from the surgical site.

5. The method of claim 4, wherein during the aspirating, the cannula is rotated at less than 420 rpm during the aspiration of the adipose tissue from the surgical site.

6. The method of claim 1, wherein the cannula is rotated by the motor clockwise and counter clockwise during the aspiration of the adipose tissue from the surgical site.

7. The method of claim 1, wherein, the cannula is rotated at less than about 200 rpm during the aspiration of the adipose tissue from the surgical site.

8. The method of claim 1, wherein the cannula is rotated using the motor without axial movement of the cannula.

9. The method of claim 1, wherein rotating the cannula using the motor connected to the removable coupler and the cannula comprises:

rotating a first gear connected to the motor; and transferring the rotation of the first gear to a second gear that is engaged with the first gear and connected to the cannula.

10. The method of claim 1, wherein venting the cannula further comprises:

allowing air to flow between the interior walls of cavity and the cannula through the venting channels.

* * * * *

UNITED STATES PATENT AND TRADEMARK OFFICE
CERTIFICATE OF CORRECTION

PATENT NO. : 8,864,747 B2  
APPLICATION NO. : 13/249113  
DATED : October 21, 2014  
INVENTOR(S) : Adnan I. Merchant et al.

It is certified that error appears in the above-identified patent and that said Letters Patent is hereby corrected as shown below:

In the Specification:

At column 5, line number 19, change "is a grove 119" to --a groove 119--

At column 6, line number 55, change "helps" to --help--

At column 7, line number 21, change "store" to --stored--

At column 8, line number 36, change "grove" to --groove-- and at line 49, change "such a motor" to --such as a motor-- and at line 58, change "tissue. They" to --tissue, they-- and at line 62, change "illustrates" to --illustrate--

At column 9, line number 10, change "5 Her08" to --508"-- and at line 36, change "illustrate" to --illustrates-- and at line 43, change "directions" to --direction-- and at line 50, change "directions" to --direction--

At column 10, line number 1, change "illustrate" to --illustrates-- and at line 9, change "directions" to --direction-- and at line 15, change "directions" to --direction--

Signed and Sealed this  
Fourteenth Day of April, 2015

Michelle K. Lee  
*Director of the United States Patent and Trademark Office*